(12) United States Patent
Vancelette et al.

(10) Patent No.: US 7,500,973 B2
(45) Date of Patent: Mar. 10, 2009

(54) CRYOSURGICAL DEVICES AND METHODS FOR ENDOMETRIAL ABLATION

(75) Inventors: David W. Vancelette, St. Louis Park, MN (US); Nicholas R. van der Walt, Hillcrest Park (ZA); Jia Hua Xiao, Maple Grove, MN (US); Eva S. Snitkin, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 441 days.

(21) Appl. No.: 11/020,791

(22) Filed: Dec. 22, 2004

(65) Prior Publication Data

US 2005/0177147 A1   Aug. 11, 2005

Related U.S. Application Data

(60) Provisional application No. 60/546,334, filed on Feb. 20, 2004, provisional application No. 60/532,420, filed on Dec. 22, 2003, provisional application No. 60/532,419, filed on Dec. 22, 2003.

(51) Int. Cl.
*A61B 18/18* (2006.01)

(52) U.S. Cl. .......................................... 606/21; 606/23
(58) Field of Classification Search .............. 606/20–26
See application file for complete search history.

(56) References Cited

U.S. PATENT DOCUMENTS

| | | |
|---|---|---|
| 3,613,689 A | 10/1971 | Crump et al. |
| 3,924,628 A | 12/1975 | Droegemueller et al. |
| 4,602,174 A | 7/1986 | Redlich |
| 4,946,460 A * | 8/1990 | Merry et al. ................ 606/24 |

(Continued)

FOREIGN PATENT DOCUMENTS

EP      0 624 347      * 11/1994

(Continued)

OTHER PUBLICATIONS

J Jones, "Mixed Gas Sorption Joule-Thomson Refrigerator," NASA Tech Briefs, vol. 15(5) May 1991, pp. 38 and 40.

(Continued)

*Primary Examiner*—Michael Peffley
(74) *Attorney, Agent, or Firm*—Jose' W. Jimenez; Kimberly K. Baxter; Gregory L. Koeller (57) ABSTRACT

A cryoablation system including a cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source. The heat exchanger may be positioned within the probe handle, within the cannula, or at least partially within the balloon. The heat transfer fluid of this cryoablation system preferably has a freezing point lower than about −110° C. and a boiling point greater than about 50° C.

11 Claims, 4 Drawing Sheets

U.S. PATENT DOCUMENTS

| | | | |
|---|---|---|---|
| 5,275,595 | A | 1/1994 | Dobak, III |
| 5,334,181 | A | 8/1994 | Rubinsky et al. |
| 5,403,309 | A | 4/1995 | Coleman et al. |
| 5,501,681 | A | 3/1996 | Neuwirth et al. |
| 5,522,870 | A | 6/1996 | Ben-Zion |
| 5,525,845 | A | 6/1996 | Beale et al. |
| 5,592,073 | A | 1/1997 | Redlich |
| 5,595,065 | A | 1/1997 | Boiarski et al. |
| 5,603,221 | A | 2/1997 | Maytal |
| 5,617,739 | A | 4/1997 | Little |
| 5,642,088 | A | 6/1997 | Unger |
| 5,644,502 | A | 7/1997 | Little |
| 5,647,868 | A | 7/1997 | Chinn |
| 5,674,218 | A | 10/1997 | Rubinsky et al. |
| 5,702,435 | A | 12/1997 | Maytal |
| 5,716,353 | A | 2/1998 | Matsuura et al. |
| 5,724,832 | A | 3/1998 | Little et al. |
| 5,741,248 | A | 4/1998 | Stern et al. |
| 5,758,505 | A | 6/1998 | Dobak, III et al. |
| 5,787,715 | A | 8/1998 | Dobak, III et al. |
| 5,891,188 | A | 4/1999 | Maytal |
| 5,901,783 | A | 5/1999 | Dobak, III et al. |
| 5,910,104 | A | 6/1999 | Dobak, III et al. |
| 5,954,714 | A | 9/1999 | Saadat et al. |
| 5,956,958 | A | 9/1999 | Dobak, III et al. |
| 6,035,657 | A | 3/2000 | Dobak, III et al. |
| 6,066,132 | A | 5/2000 | Chen et al. |
| 6,074,572 | A | 6/2000 | Li et al. |
| 6,151,901 | A | 11/2000 | Dobak, III et al. |
| 6,182,666 | B1* | 2/2001 | Dobak, III .................. 128/898 |
| 6,193,644 | B1 | 2/2001 | Dobak, III et al. |
| 6,237,355 | B1 | 5/2001 | Li |
| 6,241,722 | B1 | 6/2001 | Dobak et al. |
| 6,270,494 | B1 | 8/2001 | Kovalcheck et al. |
| 6,306,129 | B1 | 10/2001 | Little et al. |
| 6,379,348 | B1 | 4/2002 | Onik |
| 6,428,534 | B1 | 8/2002 | Joye et al. |
| 6,451,012 | B2 | 9/2002 | Dobak, III |
| 6,471,217 | B1 | 10/2002 | Hayfield et al. |
| 6,471,694 | B1 | 10/2002 | Kudaravalli et al. |
| 6,475,212 | B2 | 11/2002 | Dobak, III et al. |
| 6,530,234 | B1 | 3/2003 | Dobak, III et al. |
| 6,537,271 | B1 | 3/2003 | Murray et al. |
| 6,547,784 | B1* | 4/2003 | Thompson et al. ............ 606/21 |
| 6,569,161 | B2 | 5/2003 | Zappala |
| 6,607,545 | B2 | 8/2003 | Kammerer et al. |
| 6,706,037 | B2* | 3/2004 | Zvuloni et al. ................. 606/21 |
| 6,708,056 | B2 | 3/2004 | Duchon et al. |
| 6,709,431 | B2 | 3/2004 | Lafontaine |
| 7,101,367 | B2* | 9/2006 | Xiao et al. .................... 606/21 |
| 2001/0035189 | A1* | 11/2001 | Dobak, III .................. 128/898 |
| 2002/0045892 | A1 | 4/2002 | Kramer |
| 2002/0133148 | A1 | 9/2002 | Daniel et al. |
| 2002/0151882 | A1 | 10/2002 | Marko et al. |
| 2003/0130711 | A1 | 7/2003 | Pearson et al. |
| 2003/0199732 | A1 | 10/2003 | Suslian et al. |
| 2004/0002664 | A1 | 1/2004 | Brookner et al. |
| 2004/0002698 | A1 | 1/2004 | Hua Xiao et al. |
| 2004/0002702 | A1 | 1/2004 | Xiao et al. |
| 2004/0002703 | A1 | 1/2004 | Xiao et al. |
| 2004/0002747 | A1 | 1/2004 | Ryan et al. |
| 2004/0002748 | A1 | 1/2004 | Ryan et al. |
| 2004/0044334 | A1 | 3/2004 | LaFontaine |
| 2004/0049176 | A1 | 3/2004 | Lafontaine |

FOREIGN PATENT DOCUMENTS

| | | |
|---|---|---|
| EP | 0624347 | 11/1994 |
| WO | WO 02/04042 | 1/2002 |

OTHER PUBLICATIONS

O. Istre et al., "Oral Presentations," Journal of the American Association of Gynecologic Laparascopists, vol. 10, No. 3 Supplement, Aug. 2003, pp. S1, S12 and S13.

R. Pittrof et al., "Endometrial cryoblation using 0.9% saline as a uterine distension medium: a feasibility study," Minimally Invasive Therapy 1992: 1: pp. 283-286.

Cyril Young et al., "Out-Patient Cervical Cryosurgery," The Journal of Obstetrics and Gynecology of the British Commonwealth, vol. 79, Aug. 1972, pp. 753-755.

PCT International Search Report dated Jun. 15, 2005.

* cited by examiner

CRYOSURGICAL DEVICES AND METHODS FOR ENDOMETRIAL ABLATION

REFERENCE TO RELATED APPLICATIONS

This application claims the benefit of U.S. Provisional applications having Ser. No. 60/532,420, filed Dec. 22, 2003, entitled "DEVICE FOR TREATING ENDOMETRIAL ABLATION"; Ser. No. 60/532,419, filed Dec. 22, 2003, entitled "EXPANDABLE MEMBER WITH CIRCULATING CHILLED LIQUID FOR GLOBAL ENDOMETRIAL ABLATION"; and Ser. No. 60/546,334, filed Feb. 20, 2004, entitled "CRYOSURGICAL DEVICES FOR ENDOMETRIAL ABLATION", which applications are incorporated herein by reference in their entireties.

TECHNICAL FIELD

The present invention relates generally to cryosurgical devices for freezing and destroying biological tissues. More specifically, the invention relates to cryosurgical devices that can be used for freezing and thereby destroying endometrial tissues within the uterus of a female patient.

BACKGROUND OF THE INVENTION

Endometrial ablation is a common surgical procedure that is used to treat menorrhagia in women, which is typically accomplished through the application of either sufficiently hot or sufficiently cold temperatures to destroy the lining of the uterus. One type of procedure used for endometrial ablation involves the use of a device that rolls over the surface of the uterine wall while applying enough heat to destroy the endometrial tissue. While this type of procedure can be effective, it requires a significant amount of time and skill in manipulating the rolling device to ensure that the entire endometrium is destroyed.

Another type of procedure used for endometrial ablation also uses heat, but instead involves balloons or similar distensible bladders. These balloons are inserted into the uterus and inflated with a fluid until the balloon contacts the affected surfaces of the uterus. Fluid is then heated to an appropriate temperature to ablate or destroy the endometrium. Good surface contact is important to get complete coverage of the uterine lining. However, such coverage can be difficult due to temperature fluctuations and gradients along the surface of the balloon that can be caused by many factors, such as convective currents of the fluid within the balloon, and maintaining adequate thermal contact between the outer surface of the balloon and the uterine tissue. To improve control of the fluid temperature within the balloon, various mechanical devices and systems have been used for circulating or agitating the heated fluid, such as through multiple fluid passageways, propellers within a lumen contained within the balloon, vibrating members, and electrical impulses. These mechanical devices or systems provide varying degrees of effectiveness, depending on the administrator of the procedure and the device itself. In addition, the movement of hot fluid into the balloon can sometimes cause discomfort or possible tissue damage to the vagina and opening of the cervix as heat is conducted through the walls of the catheter to which the balloon is attached.

Another group of procedures used for endometrial ablation involves the application of extremely low temperatures and is commonly referred to as cryosurgery. In the performance of cryosurgery, it is typical to use a cryosurgical application system designed to suitably freeze the target tissue. The abnormal or target cells to be destroyed are often surrounded by healthy tissue that should be left uninjured. Many of these systems use a probe with a particular shape and size that is therefore designed to contact a selected portion of the tissue that is to be treated without undesirably affecting any adjacent tissue or organs. In one particular application used to treat conditions of abnormal uterine bleeding, cryoablation instruments and techniques are used to freeze endometrial tissue, thereby destroying at least a portion of the endometrium or lining of the uterus, while leaving the remainder of the uterus undamaged. An example of a device that can be used for this type of cryoablation is the Her Option Cryoablation System, commercially available from American Medical Systems of Minnetonka, Minnesota. In this type of system, a rigid probe is provided with a very cold tip that freezes the endometrial tissue with which it comes in contact. Where such a probe is used, the remainder of the refrigeration system must be designed to provide adequate cooling, which involves lowering the operative portion of the probe to a desired temperature and having sufficient power or capacity to maintain the desired temperature for a given heat load. The entire system must be designed so that the operative portion of the probe can be placed at the location of the tissue to be frozen without having any undesirable effect on other organs or systems. For this reason, probes in these types of systems are often in the shape of an elongated tube with a rounded tip area at one end that can be positioned within the uterus for the cryoablation procedures. Other cryocooling surgical devices, components thereof, and surgical methods are disclosed in U.S. Pat. Nos. 5,275,595; 5,758,505; 5,787,715; 5,901,783; 5,910,104; 5,956,958; 6,035,657; 6,074,572; 6,151,901; 6,182,666; 6,237,355; 6,241,722; 6,270,494; 6,451,012; 6,471,217; 6,471,694; 6,475,212; 6,530,234; and 6,537,271, each of which is incorporated by reference in its entirety.

In many cases, the cold portion of an instrument or device is provided through the use of a Joule-Thompson refrigeration system. These refrigeration systems generally operate through the expansion of a high-pressure gas through an expansion element that includes some sort of a flow restrictor. The restriction of flow may be accomplished through the use of a small orifice, a narrow capillary tube, or some other sort of passage that is smaller than the supply source through which the high-pressure gas must move. Typically, the refrigeration system includes a source of high-pressure gas, a heat exchanger, an expansion element, a heat transfer element, and various tubes or conduits to allow movement of the gas from one component to another. The high-pressure gas passes through the heat exchanger to lower the gas temperature at least slightly, then the gas temperature is further lowered through the isenthalpic expansion of the gas as it passes through the expansion element. This expanded and cooled gas is exposed to the heat transfer element, where the gas can then absorb the heat that has been transferred from the environment.

Joule-Thompson refrigeration systems can be either open loop systems or closed loop systems, both of which include features that are advantageous for different applications. With open loop systems, the gas is exhausted to the atmosphere after expansion and heat absorption. The source of the high-pressure gas in this type of system is usually a high-pressure gas cylinder from which the gas is depleted over the course of multiple cycles of the refrigeration system. These open loop systems are relatively tolerant of a certain amount of contamination from outside sources, such as water or oil, which can selectively collect at the flow restriction where the majority of the cooling occurs. This is because any such contaminants that enter the open loop systems can be exhausted from the system along with any gas that is exhausted from the system to the environment. Thus, if system joints are broken or separated for any reason, such as during the replacement or repair of parts, contaminants will often be flushed from the system along with the exhaust of gas.

In contrast, closed loop Joule-Thompson refrigeration systems involve repressurizing and circulating the gas in the system after expansion. That is, the high pressure gas is expanded through the expansion element, the gas is exposed to the heat transfer element where heat is absorbed, and then the lower pressure gas is returned to a compressor that can be used to repressurize the gas. The gas is not exhausted from the system, but is instead recirculated back through the heat exchanger and the expansion element. Therefore, any contaminants that are unintentionally introduced into the system can collect within the system over a period of time and may undesirably be deposited within the system in such a place that eventually blocks or partially blocks the unrestricted flow of gas through the system. Thus, these closed loop systems may be provided as permanently sealed systems that are designed to prevent the introduction of contaminants, which also results in a system in which parts cannot easily be removed or replaced. It is known to use self-sealing couplings in such systems; however, the sealing provided by such systems is limited and typically still allows some contaminants to enter the system. For example, the couplings in such a closed loop system may include threaded fittings that do not provide for repetitive disconnection and reconnection without the chance of at least some small amount of contaminants entering the system.

These closed loop Joule-Thompson refrigeration systems can thus be complicated to use for surgical devices, such as cryosurgical probes, when it is desirable to use multiple tips or connectors for the same or different surgical techniques. In particular, such devices typically have a compressor connected to the probe, where the probe consists generally of a handle, a cannula, and a cold tip. A heat exchanger is typically located within the handle, and the expansion element is typically located in the cold tip. The probe cannula or cold tip is desirably interchangeable with various shaped tips or devices to perform various surgical techniques, such as techniques requiring tips that are flat, cylindrical with various diameters, or sharp-edged. In addition, the cold tips must be capable of being sterilized for use in surgical techniques, to allow for repeated use of the system with the same or different tips.

In most systems, the cooling tip is designed or chosen to be small enough to easily be accurately positioned at the treatment area, which generally limits the technique to applying the cooling to a relatively small area with each placement of the probe. The entire process thus typically requires that the probe be positioned at least two or three times to ablate the entire target area, such as an entire uterine cavity. Each relocation of the probe requires repetition of the same cooling steps, which can be time consuming and requires multiple precise placements of the probe to guarantee that the entire area is adequately ablated.

With these cryosurgical techniques, it is typically desirable to insulate the shaft of a cryosurgical probe to prevent the unintentional freezing of tissue at locations along the length of the probe that may inadvertently or unavoidably come in contact with the probe shaft. One way these shafts are often insulated is to provide a vacuum space along the probe shaft. This method is sometimes ineffective because the level of the vacuum maintained in such a space can degrade over time due to the outgassing of metals, plastics, and braze joints. This outgassing can increase during sterilization procedures in which heat is applied to the probe. Thus, it is known to incorporate the insulation into a disposable sheath that can be disposed over a probe, as is described in U.S. Pat. No. 6,182, 666 (Dobak III), for example, so that the disposable element is not subjected to repeated sterilization, but instead can be discarded without significant degradation of the insulation. This disposable sheath can be constructed of a thermally resistive material, such as a plastic, to inhibit heat transfer between the surrounding tissues and the probe that it covers.

There is, however, a need to provide a system and device for endometrial ablation using cryosurgical methods that improve the overall coverage of the endometrial surface for a range of uterine sizes and shapes while maintaining an appropriate depth of ablation. There is further a need for these systems and devices to be easily manipulated to the affected areas, while having the ability to quickly generate an appropriately sized cold area or ice ball within the uterus for ablation. In addition, these systems will desirably include disposable and/or interchangeable portions to increase the number of uses of some components of the system and will desirably include more efficient ways of cooling the gases and/or fluids used in the system.

SUMMARY OF THE INVENTION

The present invention provides systems and methods of performing endometrial ablation using cryoablation techniques that include inserting a device through the cervix, where it is deployed to expand or otherwise spread out within the uterine cavity to provide uniform freezing of the entire surface of the cavity. The inserted device may include removable cooling tips that can be fluidly coupled and decoupled from the handle of the device, such as an expandable balloon or a multi-fingered extension.

In one aspect of this invention, a modular cryoablation system for performing endometrial ablation is provided, the system including an elongated tubular cannula having a proximal end, a distal end, and a longitudinal axis, and a probe tip comprising at least two extensions that are each expandable and retractable outwardly relative to the longitudinal axis of the cannula and that each comprise an internal fluid path or are conductively coupled to the probe tip, wherein the probe tip is either detachably or permanently coupled to the distal end of the cannula. A probe handle extends from the proximal end of the cannula and is in fluidic communication with the internal fluid path of each of the extensions through the cannula, and a source of compressed refrigerant is fluidly connected to the probe handle. The probe tip may further include a sheath that can at least partially contain at least one extension in a retracted position, wherein the sheath can be moveable along the length of the cannula to deploy the at least one extension from its retracted to its expanded position. The probe tip may be disposable, removable, and/or replaceable.

The probe tip of the system may be coupled to the cannula by a coupling mechanism that fluidly isolates the fluid paths of the extensions from the probe handle and refrigerant source to create a closed first fluid system when the probe tip is detached from the cannula. The coupling mechanism may further allow for fluidic communication between the probe handle and the probe tip through the cannula when the probe tip is attached to the cannula.

In another aspect of the invention a cryoablation system is provided including an elongated tubular cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source. The balloon is preferably expandable in response to an addition of a volume of heat transfer fluid. The heat exchanger may be positioned within the probe handle so that the secondary refrigerant can cool the heat transfer fluid to a treatment temperature before the heat transfer fluid is provided to the balloon, or the heat exchanger may alternatively be positioned within the console of the system so that the secondary refrigerant can cool the heat transfer fluid to a treatment temperature before the fluid is provided to the probe handle, or the heat exchanger may alternatively be positioned within the cannula so that the secondary refrigerant can cool the heat transfer fluid to a treatment temperature before the heat transfer fluid is provided to the balloon. In another alternative, the heat exchanger is positioned at least partially within the balloon. The heat transfer fluid of this cryoablation system preferably has a freezing point lower than about $-110°$ C. and a boiling point greater than about 50° C., and more preferably has a freezing point lower than about $-130°$ C. and a boiling point greater than about 60° C. In any case, the heat transfer fluid preferably has a boiling point greater than the operating temperature of the system so that the heat transfer fluid does not vaporize during or after operation of the system. Alternatively, the heat transfer fluid may be of a type that will vaporize, if desired.

The present invention further includes a method of performing endometrial ablation, comprising the steps of providing a cryoablation system comprising a tubular cannula having a proximal end and a distal end, a balloon extending from the distal end of the cannula and fluidly connected to a source of heat transfer fluid through the cannula, a pump for circulating the heat transfer fluid into and out of the balloon, a probe handle extending from the proximal end of the cannula and in fluidic communication with the balloon through the cannula, and a heat exchanger for varying the temperature of the heat transfer fluid, then inserting the balloon in a collapsed state into the uterus of a patient. The balloon is then inflated with a volume of the heat transfer fluid at a first temperature until it reaches a predetermined size and the heat transfer fluid is cooled with the heat exchanger to lower its temperature from first temperature to a desired treatment temperature. The balloon is maintained in this position within the uterus for a therapeutic time period, then the balloon is deflated until it is sufficiently small to allow for its removal from the uterus, at which point the balloon is removed from the uterus.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
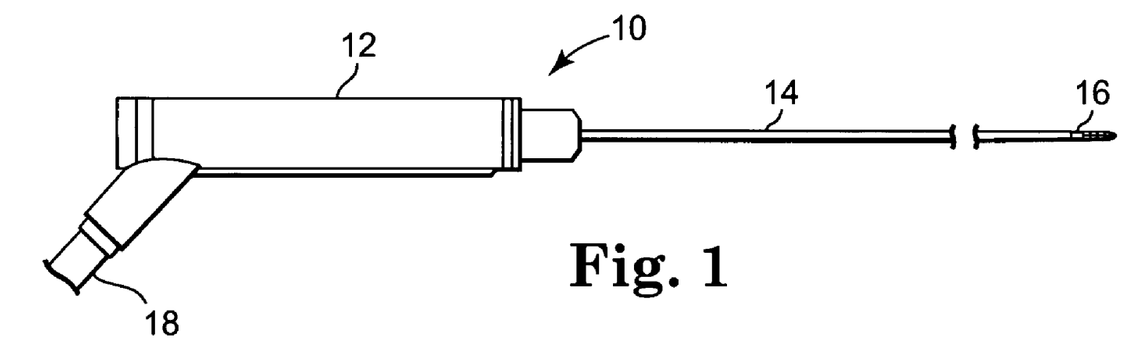
FIG. 1 is a front schematic view of a cryosurgical probe of the type that may be used in accordance with the cooling devices and methods of the present invention.

Referring now to the Figures, wherein the components are labeled with like numerals throughout the several Figures, and initially to FIG. 1, one configuration of a cryosurgical probe 10 that can be used for cryoablation of endometrial tissue in the uterus of a female patient is shown. The probe 10 generally includes a handle 12, a hollow tubular cannula 14, and a cold tip 16. The handle 12 can be metallic to facilitate effective sealing of the components to minimize any gas or fluid leakage that might otherwise occur. The handle 12 can also be provided with insulating properties so that it is comfortable for the user to manipulate, such as may be provided by the inclusion of insulation (e.g., aerogel) in the handle or in the form of a vacuum space within the handle. Several components of the refrigeration system, such as heat exchangers, can optionally be housed within the handle 12, as will be discussed in further detail below. Other components may also be housed within the handle 12, such as various auxiliary instruments to support items such as temperature sensors, heaters, illumination optics, viewing optics, laser optics, and ultrasonic transducers. A conduit 18 preferably extends from the end of the probe 10 opposite the tip 16, which may contain tubing for refrigeration system materials, insulation materials, power cables for any electrical components, fiber optical cables to support illumination, viewing, and laser components, and the like.

The cannula 14 may include within its hollow opening other components of the refrigeration system, such as a high-pressure conduit to transport a high-pressure gas mixture from the handle 12 to the cold tip 16 and a low-pressure conduit to return the expanded gas mixture from the cold tip 16 back to the handle 12. Other components of the refrigeration system, such as a Joule-Thompson expansion element, can be housed within the cold tip 16. When a Joule-Thompson expansion element is used for the cryoablation procedures of the present invention, a cold tip or some element located near the cold tip preferably includes at least one small opening that allows passage of a pressurized gas, such as nitrous oxide, carbon dioxide, or a mixed gas from an inner channel to a space having a larger volumetric capacity. As the gas expands rapidly, it chills to temperatures that are sufficiently low to perform low-temperature surgical techniques. In cases where material flowing through the cannula 14 is at a low temperature, the cannula 14 is preferably designed to minimize heat transfer from the surrounding tissues to the cryogenic gas mixture and to also keep the cannula 14 from unintentionally freezing tissue that comes in contact with its outer surfaces. Thus, the cannula 14 can be formed of a thermally resistive material, such as a rigid plastic, or it can be formed of a metal having vacuum or other insulation provided internally or externally to inhibit heat transfer. The cannula 14 may be a rigid tube or it can be more flexible and shaped differently than shown and/or vary in shape and size along its length.

Figure 2:
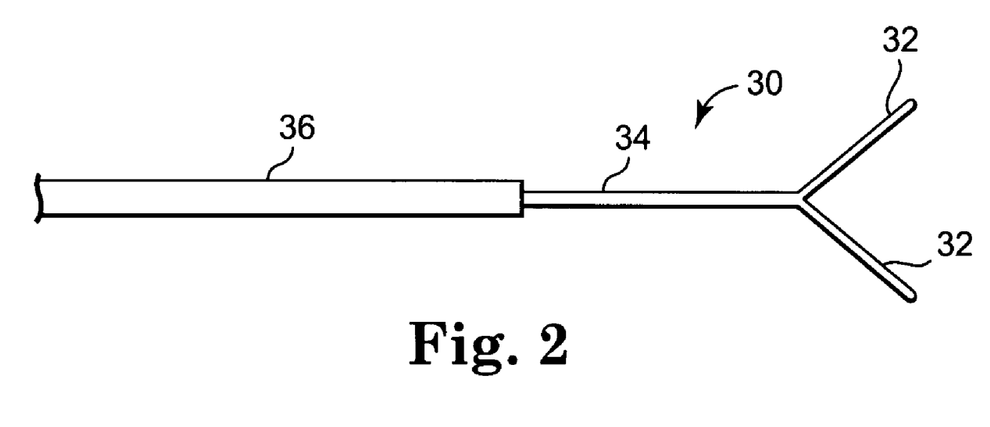
FIG. 2 is a front schematic view of one embodiment of a cooling tip and sheath for use with cryoablation in accordance with the invention.

In accordance with the present invention, the cold tip 16 is shown generally in FIG. 1 as an elongated tube with a rounded tip portion, but may be provided in a number of different forms as will be described in further detail below. One alternative embodiment of a cold tip of the invention is illustrated in FIG. 2 as a passive thermally conductive extension 30 that extends from the cooling portion of the probe. As shown, the extension 30 includes two legs 32 that extend outwardly in a general V-shape from a center tube 34. The legs 32 are preferably hinged at their attachment point to center tube 34 to allow their movement toward the longitudinal axis of the tube 34 during insertion and retraction of the probe through the cervix. Preferably, the probe to which the extension 30 is attached includes a device or is otherwise configured to provide for the collapse and expansion of the legs 32 when desired. It is possible that the legs 32 rotate in either direction so that they either move toward each other and toward the center tube 34, or so that they move toward each other in the direction that would essentially close the V-shaped space between them. Alternatively, they can rotate in opposite directions from each other. The connection between the legs and the probe increases thermal conductivity between the components through the use of a biocompatible, thermally conductive medium and/or intimate contact between the two components. The hinge mechanism may further include a spring element that forces the legs apart when deployed.

In any case, the cryosurgical probe to which the extension 30 is attached preferably includes a mechanism that will be at least partially located external to the patient for controlling the movement of the legs 32 when they are inside the uterus. In this way, the legs 32 can be collapsed when the probe is being inserted into the uterus, thereby minimizing the external dimensions of the device. The legs 32 can then be deployed by the external mechanism to rotate outwardly to their desired positions once they are located within the wider space of the uterus. This mechanism may comprise a sheath 36 that at least partially covers the center tube 34 and that can contain the legs 32 in their collapsed position during insertion of the device. The sheath 36 can then preferably be withdrawn or slid in a direction away from the legs 32 to thereby release the legs 32 and allow them to rotate to their desired positions to perform the surgical procedure. After the uterine ablation procedure is complete, the sheath 36 may then be slid back toward the legs 32 to collapse the legs and withdraw the device. Alternatively, the sheath 36 can be held in a stationary position relative to the patient while the device is pulled outward from the body, thereby causing the legs 32 to collapse into the sheath 36, after which the entire device (including the sheath 36) can be withdrawn from the uterus. The extension 30 may further include hinged or flexible copper elements that originate at the outside diameter of the center tube 34 and spread laterally toward the cornua when inserted in the uterus.

Figure 3:
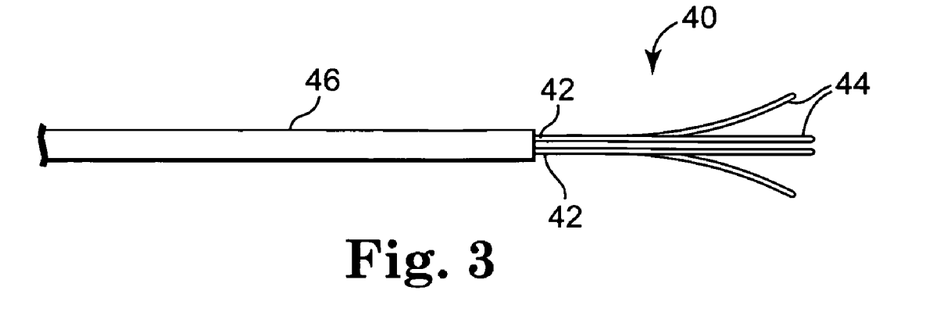
FIG. 3 is a front schematic view of another embodiment of a cooling tip and sheath for use with a cryosurgical probe.

Another alternative embodiment of a cold tip of the invention is illustrated in FIG. 3 as a multiple-fingered extension or cold tip 40 that extends from the cooling portion of the probe. The extension 40 includes two elongated members 42 that extend directly from the end of the probe, each of which branches into two separate flexible fingers 44. The flow of refrigerant to these fingers 44 is preferably split into separate flow paths to provide cooling within each individual finger 44, such as with elongated tubing that extends into each of the flexible fingers 44. Alternatively, each of the fingers 44 can have a physical interior structure that directs the refrigerant flow from each elongated member 42 to each of the fingers 44 that extend therefrom to provide the necessary cooling to the fingers 44. In this way, each finger 44 is supplied with direct cooling from the refrigerant. It is further possible that the refrigerant flow is not specifically divided for each of the elongated members 42, but that the flow is a single path that extends through the cooling portion of the probe to the point where the extension 40 is attached. Interior channels within the extension 40 can then cause the physical distribution of the refrigerant to the elongated members 42 and the fingers 44 that extend therefrom. It is further contemplated that each finger has its own valve for controlling the refrigerant, or that the refrigerant for multiple fingers can be controlled by a smaller number of valves (e.g., four fingers are controlled by one or two separate valves). These valves may be located at the base of the fingers, or at some point along the length of the fingers.

The fingers 44 are preferably constructed in such a way that they will fan out into a generally triangular shape when not constrained against a bias that tends to push them away from each other. In other words, the fingers 44 are preferably configured to be "spring loaded" so that they tend to move outwardly from the longitudinal axis of the extension 40. To that end, the extension 40 may also include a sheath 46 that at least partially covers the extension 40 and contains the fingers 44 in their collapsed position during insertion of the device, then the sheath 46 can be withdrawn or slid relative to the fingers 44 to thereby release the fingers 44 and allow them to splay outwardly so that the outermost fingers can contact the uterine wall. The fingers 44 may be constructed of stainless steel or nitinol or other materials that are sufficiently conductive and elastic to facilitate heat transfer and outward splaying. The fingers 44 may be designed so that they move away from each other generally in one plane, or can be designed so that they can move in more than one plane relative to each other to contact the uterine wall surfaces. After the ablation is complete, the extension 40 can be slid relative to the sheath 46 to collapse the fingers 44 and withdraw the device from the uterus. The sheath 46 may further be provided with insulating properties so that it can provide control of the freeze length when it is slid along the length of the extension 40 relative to the fingers 44. A sheath that is insulated can greatly improve the system performance by minimizing heat transfer from the patient to the fluid within the fingers and probe, along with protecting against unintentional freezing of body tissues. The extension 40 may further include a sterile barrier between the fingers 44 and the patient, such as a thin membrane or cover that covers the fingers 44. The membrane may be filled with a benign fluid, such as propylene glycol, or may be evacuated during freezing.

Figure 4:
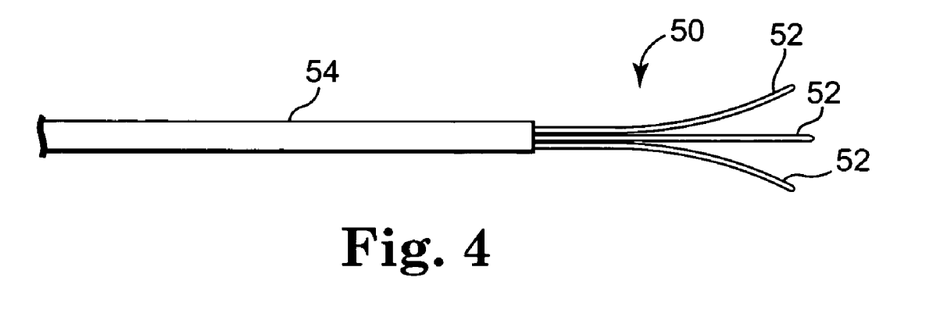
FIG. 4 is a front schematic view of another embodiment of a cooling tip and sheath.

The number of elongated members and the number of flexible fingers that branch from each of the elongated members can vary from the two members and two branching fingers illustrated in FIG. 3, such as is shown in the arrangement of FIG. 4. In this embodiment, an extension or cold tip 50 includes three distinct flexible finger portions 52 that extend from the cooling portion of the probe. The extension 50 may have three or more internal refrigerant flow tube or passages, each with its own refrigerant flow, or multiple elongated members may extend from the cooling portion of the probe, each having more or less than two extending fingers. The number of fingers from each elongated member may be the same or different than the number of fingers extending from other elongated members within a single system, if desired. This embodiment may also include a sheath 54 that can compress the finger portions 52 toward each other during insertion and removal of the device, yet allow the finger portions to move outwardly into a generally triangular-shaped shape to perform the cryosurgical procedure, similar to the sheath movements described above relative to FIG. 3. Alternatively, a single supply line may branch into multiple fingers.

Figure 5:
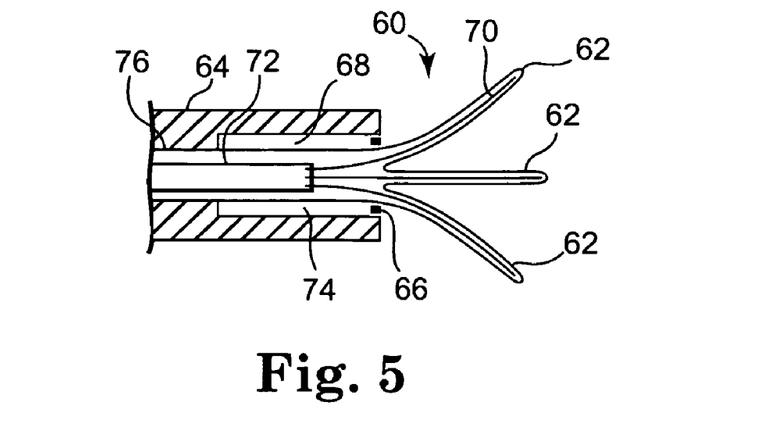
FIG. 5 is a front cross-sectional view of an end portion of a cooling tip and sheath as used with a trifurcated tip extension.

FIG. 5 illustrates an enlarged cross-sectional view of a portion of a cooling tip of the present invention, which is similar to the type of extension shown in FIG. 4. In particular, a cooling tip 60 includes three capillary tube impedances 70 inside fingers 62, coupled together at a distance away from their distal ends and joined to a high pressure side of the base system primary refrigerant circuit. The fingers 62 preferably each include a capillary tube 70 extending from the end of an inner supply tube 72 toward the ends of the fingers 62. The capillary tubes 70 can carry refrigerant that is provided by the supply tube 72, and expand it into each of the fingers 62 to provide an acceptable treatment temperature for performing the ablation procedure.

The fingers 62 preferably have a bias to move outwardly from the center axis of the device, and are at least slightly spaced from one another in a generally W-shaped pattern when deployed. The cooling tip 60 preferably further includes an insulating sheath 64 that is sized to compress the fingers 62 toward each other when slid along the longitudinal axis of the tip. The outer diameter of the sheath 64 is chosen to fit within the cervical canal of the patient and has a large enough internal cavity or channel to be able to contain the extending fingers. As shown, the sheath includes an inner channel 68 that has a wider portion 74 at the end closer to the free or distal end of the fingers 62 to allow for containment of the fingers 62 when desired. The narrower portion 76 of the channel 68 that is spaced further from the free or distal end of the fingers 62 is preferably too small to accommodate the fingers 62 and therefore provides a stop that limits the movement of the fingers 62 when they are withdrawn into the cooling tip 60. For example, the sheath 64 can be designed so that when the fingers 62 are in their retracted position, the majority of the lengths of the fingers 62 are enclosed within the wider portion 74 and at least the tips of the fingers 62 extend at least slightly beyond the end of the sheath 64 so that the fingers 62 remain properly positioned relative to each other during retraction and deployment and are not obstructed by the channel 68 in any way.

The cooling tip 60 may further include a cap 66 at one end of the sheath 64 that generally joins the fingers 62 to the small outer dewar wall of the sheath 64. The cap 66 may include a number of openings that correspond to the number of fingers 62 included in the tip 60, such that this embodiment would include a cap 66 having three openings to correspond to the three fingers 62 of the cooling tip. These openings can maintain the fingers in their desired spacing and arrangement relative to each other within the cooling tip 60. In other words, the positioning of the cap 66 preferably prevents the fingers 62 from slipping so far into the sheath 64 that the solid portion of the cap 66 obstructs the fingers 62 when it is desired to deploy the fingers.

As shown in FIG. 5, the outer layer of the fingers 62 is formed as a single piece that connects all of the fingers 62; however, each of the fingers may be discrete pieces that are arranged relative to each other as provided by the invention. In one example of a cooling tip, the two outermost fingers can be spaced from each other by about 3 cm at their distal ends, with the middle finger extending generally halfway between them, and the middle finger can have a length that is about 5 cm for freezing in a 8 cm uterus. These dimensions and spacing can be considerably different from this, however, and can be particularly designed or chosen for each individual patient.

The cooling tip 60 may optionally include a heater wire and thermocouple wrapped around at least one of the fingers 62. After the cryoablation process is completed, the heater wire can be activated to facilitate removal of the fingers 62 from the treated area by at least slightly heating the ice ball that has formed around the cooling tip. At this point, the sheath 64 can be moved relative to the fingers 62 to recapture them within the sheath 64 before removing the entire tip 60 from the uterus. Other methods of heating the fingers is also possible, such as providing a heated fluid in a primary or secondary refrigeration circuit.

With any of these multi-fingered probe extensions, a recuperative heat exchanger is preferably used for a primary refrigeration circuit to cool the fingers for the ablation process. This heat exchanger may be located within the control handle, or at some location between the control and refrigerant supply console and the system handle. Alternatively, the heat exchanger may be located within the cool tip portion of the probe. The portions of the probes that are used for the ablation process are preferably conductive, while the remainder of the probe is preferably insulated to prevent unwanted freezing of surrounding tissue that comes in contact with probe components. In addition, any of the cooling tips of the invention that include multiple fingers or extending features may include a means for heating the tips to melt them free of the endometrium after the freezing procedure is complete, thereby allowing for removal of the device from the uterus.

Figure 6:
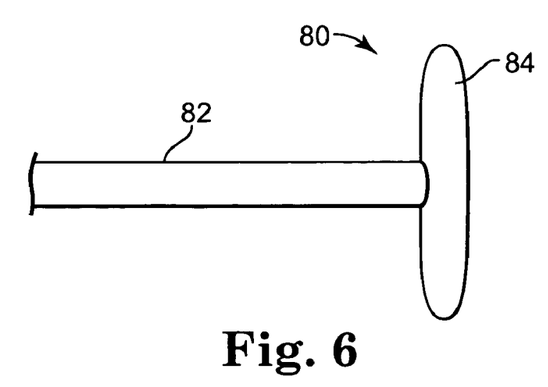
FIG. 6 is a front schematic view of an embodiment of a cooling tip in a T-shape for use with a cryosurgical probe.
Figure 7:
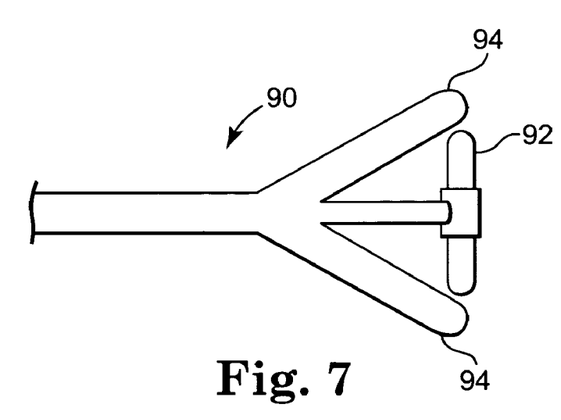
FIG. 7 is a front schematic view of an embodiment of a cooling tip in a combination T-shape and Y-shape for use with a cryosurgical probe.

FIG. 6 illustrates another embodiment of a cold tip 80 in accordance with the present invention. Cold tip 80 generally comprises an elongated portion 82 with a cylindrical bar 84 at one end to form a T-shaped extension. For one example, the cold tip 80 includes a cylindrical bar 84 that is 30 mm long with a 5 mm diameter that is attached to the end of a copper disposable tip that is 45 mm long. FIG. 7 illustrates a cold tip 90 that also uses a T-tip extension in the form of a cylindrical bar 92, similar to the cylindrical bar 84 of FIG. 6; however, the cold tip 90 also includes two extending legs 94 in a Y-shaped configuration that provides additional cooling surfaces for the cryosurgical procedure. With both of these cold tips 80, 90, the portions that extend beyond the main tube provide additional surface area that can reach a larger portion of the endometrium with a single placement of the cryosurgical probe to perform the ablation procedure more efficiently.

Another alternative embodiment of a cold tip of the invention includes a balloon with circulating fluid and local cooling. In particular, this embodiment includes an intermediary heat transfer fluid that distributes cooling from the cold tip of the probe to the uterine wall. The balloon is inserted in its deflated state into the uterus through the cervix. The balloon is then filled with a heat transfer fluid to expand the balloon within the uterine cavity to contact the uterine wall. Preferably, the amount of pressure used is minimized so as to not put unnecessary amounts of pressure on the uterus. The fluid within the filled balloon can also be provided with an impeller to transfer the cooling by convective heat transfer from the cold tip of the probe to the walls of the balloon. Preferably, the cold tip of the probe and the impeller are energized during the filling of the balloon with fluid, thereby generating and circulating a flow of extremely cold fluid within the balloon. This causes rapid freezing of the endometrium via conduction through the balloon material. Sensors may be provided to measure the temperature and pressure of the fluid within the balloon. Preferably, the internal design of the probe tip may be designed to maximize the cooling power and lower the tip temperature during the procedure. In addition, the balloon preferably fully encloses the cold tip. This design may further include a sheath that at least partially covers and contains the balloon in its collapsed position during insertion of the device, after which the sheath can be withdrawn or slid in a direction away from the balloon to thereby release balloon and allow it to expand outwardly to contact the uterine walls. The sheath may further be provided with insulating properties so that it can provide control of the freeze length when it is slid along the length of the extension relative to the balloon.

The balloon embodiment of the cold tip described above may further optionally include insulated lines through which the cold fluid can circulate to and from a console that provides the refrigerant. That is, the refrigerant can be cooled to therapeutic temperatures within the console rather than being cooled locally within the uterus. This system consists generally of a hand piece, a balloon, various sensors, fluid lines, and a coupling to the console. A cooler, valves, pumps, and reservoirs are housed within the console. The console may also have the ability to supply the balloon with warm heat transfer fluid to allow thawing of tissue subsequent to freezing and to allow easier removal of the probe. Thus, the console includes the necessary internal cooler and fluid handling circuitry for it to perform as a generator of warm or chilled heat transfer fluid. The system is preferably also provided with a control system to regulate the flow of heat transfer fluid to and from the balloon and to control the pressure within the balloon. When the temperature of the refrigerant is lowered outside the uterus, it is further preferred that a sheath be provided with insulating properties to keep the cooling portion of the tip from ablating the cervical canal when the probe is being inserted through the cervix to the uterus.

Figure 8:
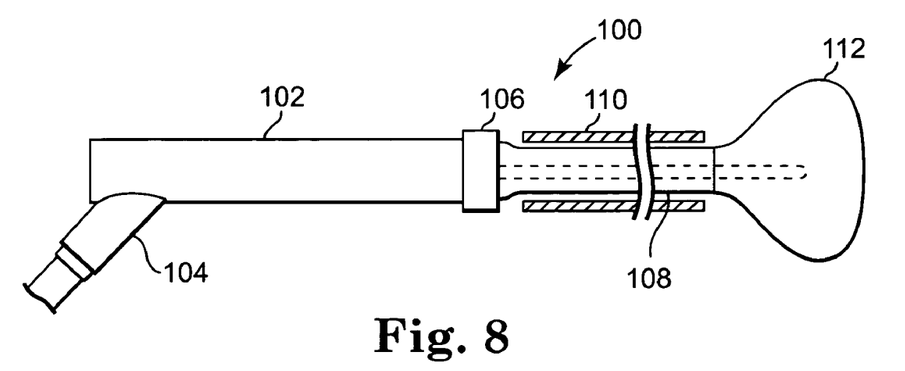
FIG. 8 is a front schematic view in partial cross-section of a cryosurgical probe including an expandable portion and a sheath that allows for inflation and compression of the expandable portion.

FIG. 8 illustrates one embodiment of a cryosurgical probe 100 that generally includes a handle 102 having a conduit 104 extending from one end of the probe 100 opposite a coupling 106. The conduit 104 may contain tubing for refrigeration system materials, power cables for any electrical components, fiber optical cables to support illumination, viewing, and laser components, and the like. Probe 100 further includes an elongated cannula 108 extending at a first end from the coupling 106 and a sheath 110 that extends along at least a portion of the length of the cannula 108. A balloon 112 is attached to the second end of the cannula 108 and is shown in this figure in its deployed or partially expanded condition. The sheath 110 is moveable along the length of the cannula relative to the balloon 112 to compress and deploy the balloon 112, as desired. That is, the sheath will be at least partially retracted from the balloon 112 when it desired to inflate the balloon 112 to treat the patient, then the probe 100 can preferably provide a volume of fluid into the balloon 112 so that it is at least slightly pressurized. The fluid provided to the balloon 112 may be provided through the conduit 104, which may be connected to a relatively small volume of fluid, such as a portable tank that can provide fluid under pressure, or may be connected to a relatively constant source of fluid that is compressed on site and provided to the probe 100 through a supply line.

The balloon 112, cannula 108, and any protective sheath that may be provided over the balloon 112 may be components of a disposable probe system that couples to a cryoablation system probe handle. The coupling mechanism, such as coupling 106, preferably includes a mechanism for sealing all fluid circuits in the system from the ambient environment when the probe is detached. A device or system is also preferably provided to lock the handle to the probe during operation of the system. Again, the components of the system that are not intended to be used at a low temperature are preferably insulated to minimize the refrigerant loss during operation.

One preferred method of performing cryoablation in accordance with the invention includes attaching the balloon 112 in a deflated condition to the handle 102 through the coupling 106. As described above, the balloon may be part of a disposable probe system that also includes at least a cannula 108 to which the balloon 112 is attached. In any case, the balloon 112, which may be compressed within the sheath 110, is then inserted into the patient. The balloon 112 is then inflated with a fluid that is relatively warm until the balloon is contacting all of the uterine surfaces that need to be ablated. The balloon is preferably at least slightly pressurized at this point. The warm fluid within the balloon 112 is then replaced with cold fluid through the use of a heat exchanger, as described below. Once the fluid reaches its low cryoablation temperature, the endometrium is frozen to the desired thickness. The cold fluid is then replaced with warm fluid, which can again be accomplished through the use of a heat exchanger, until the balloon is sufficiently de-iced to allow it to break free of the frozen tissue. The balloon 112 can then be allowed to collapse and optionally be compressed again within the sheath 110 for removal of the probe 100 from the patient.

Figure 9:
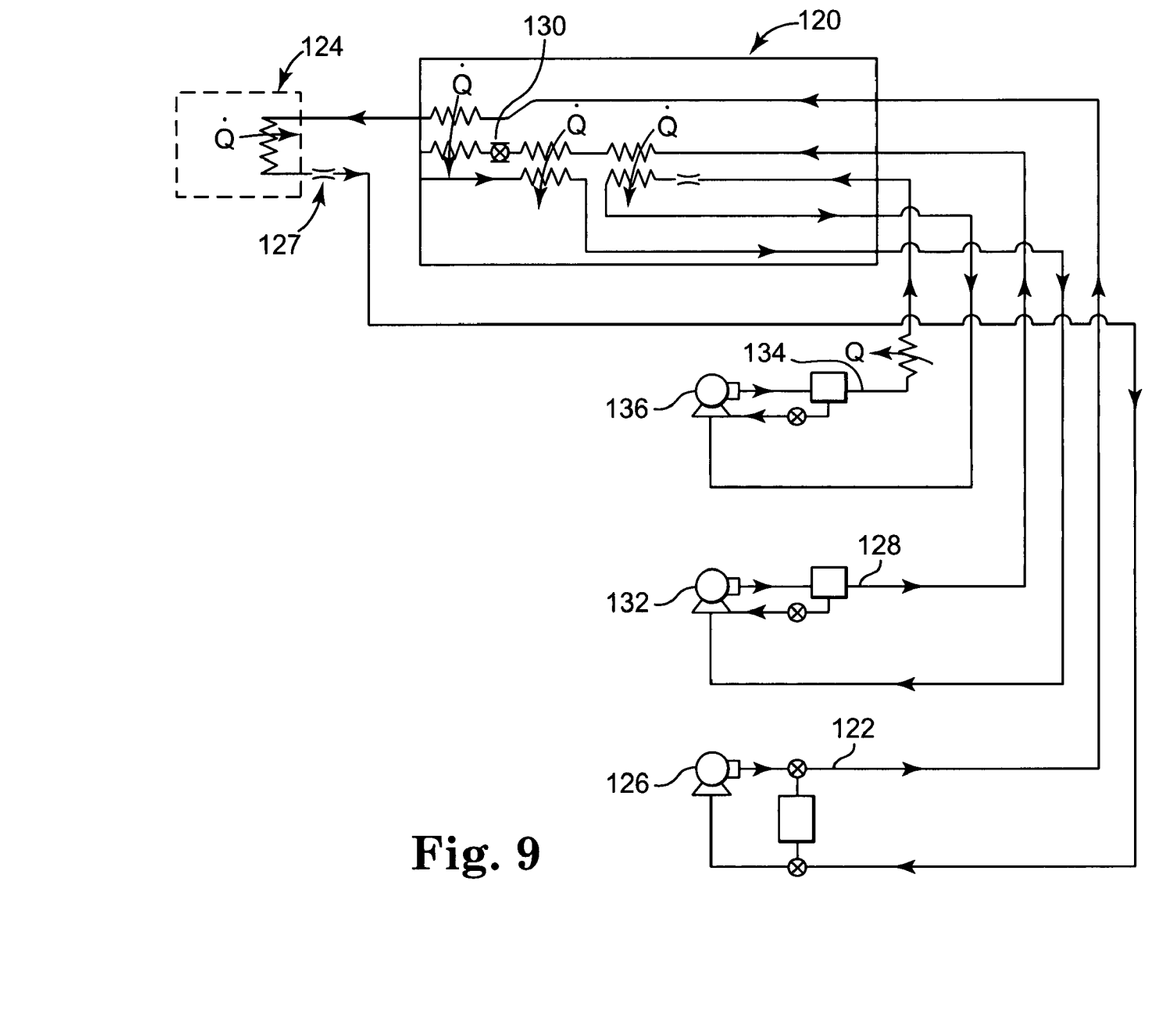
FIG. 9 is a schematic view of refrigeration circuits and their primary components used for providing fluids and changing the temperatures thereof for a cryosurgical probe in accordance with the present invention.

The probe 100 or the system of which it is a part further preferably includes a heat exchanger that may be provided in one of several locations in the system. These heat exchangers preferably operate with the use of a primary refrigeration circuit containing a first fluid and a secondary refrigeration circuit containing a second fluid, where both fluids simultaneously circulate through the heat exchanger to change the temperature of the fluids until a desired temperature of one or both fluids is achieved. In one embodiment, the heat exchanger can be located in the console, where the first fluid is cooled through Joule-Thompson expansion. Cooling of the first fluid may include a separate closed loop, precool circuit as shown in FIG. 9, or may include a single compressor and refrigerant circuit. The second fluid is cooled in the heat exchanger within the console by the extremely cold temperature of the first fluid, and then delivered to the balloon by way of a closed loop pumping circuit. This heat exchange process will thereby cool the second fluid to the temperature necessary for cryoablation. In another embodiment, the heat exchanger is located within the handle of the probe where the first fluid is again cooled through Joule-Thompson expansion, and again the second fluid is provided as a warm fluid to the balloon through a separate fluid path. The second fluid in this embodiment only needs to circulate around the comparatively shorter path between the balloon and the handle of the probe until the warm second fluid is cooled in the heat exchanger within the handle by the extremely cold temperature of the first fluid. This heat exchange process also cools the second fluid to the desired cryoablation temperature. In both of these embodiments, the components in which the tubing is located should be insulated to provide efficient heat transfer without any undesired heating from the surrounding tissue, for example.

In another embodiment, the heat exchanger is located within the balloon itself. As with the other embodiments, the first fluid is cooled through Joule-Thompson expansion and the second fluid is provided as a warm fluid to the balloon through a separate fluid path. In this case, the heat exchanger is preferably at least small enough to fit through the cervical canal, along with the balloon, cannula, and any other attached components. Because the cooling of the fluid within the balloon occurs more directly when the heat exchanger is located within the balloon, the cooling process can be comparatively quicker and can require less insulation of the other components of the device.

FIG. 9 is a schematic view of a system used for endometrial cryoablation using circulation of chilled liquid into and out of a balloon in a uterine cavity in accordance with the present invention, where a probe handle 120 is schematically represented as enclosing a portion of three fluid circuits. Alternatively, the heat exchange and refrigerant expansion components of the circuits shown in the probe handle could be located within the system console. The first fluid circuit is a heat transfer fluid circuit 122 that circulates a heat transfer fluid that remains a liquid throughout the ablation process, which heat transfer liquids are described in further detail below. The circuit 122 circulates the heat transfer liquid with the use of a pump 126 through the balloon 124 to perform the actual cryoablation. The circuit 122 further includes a small restriction 127 in the flow path to provide a slight pressurization of the balloon 124. A second fluid circuit is the Joule-Thompson circuit or primary refrigeration circuit 128, which cools the heat transfer fluid in a heat exchanger prior to where the heat transfer fluid enters the balloon 124. The actual Joule-Thompson expansion occurs in an expansion device 130 immediately upstream of the heat exchanger. This circuit 128 is driven by a compressor 132.

A third fluid circuit is the precooler circuit or secondary refrigeration circuit 134. In this circuit 134, the refrigerant in the circuit 128 is compressed and condensed prior to entering a precool heat exchanger, where it removes heat from the primary Joule-Thompson refrigeration circuit 128. Circuit 134 is preferably a conventional vapor compression cycle, such as is used in a household refrigerator and preferably operates in an evaporator temperature of about −50° C. By precooling the Joule-Thompson fluid, the cooling power of the Joule-Thompson circuit 128 is greatly increased at lower power ratings, thereby providing the extremely low (e.g., −100° C.) temperatures needed for a practical endometrial ablation device. This circuit 134 is also driven by a compressor 136. The precooler circuit 134 can be run constantly, the heat transfer fluid circuit 122 can be run to deploy the balloon 124, and if the Joule-Thompson circuit 128 is operated concurrently, cryoablation can occur.

The heat transfer fluids used in accordance with the present invention may include a variety of fluids that can provide the necessary cooling and heating of the tip of the device. The fluid is preferably biocompatible so that any unintentional fluid leaks would not be dangerous to the patient. Exemplary fluids include a hydrofluorocarbon fluid, such as Dupont Vertrel XF, which is commercially available from DuPont Fluorochemicals of Wilmington, De.; a 1-mehosyheptafluoropropane, such as Novec HFE-7000, which is commercially available from the 3M Company of St. Paul, Minn.; a perflurocarbon or perfluorohexane, such as F2 Chemicals Flutec T14 (PF-I-hexane) or PP1 (PF-n-hexane) or combination, which is commercially available from F2 Chemicals Ltd. of the United Kingdom; ethyl alcohol (ethanol) (e.g., alcohol denatured with IPA and MeOH), which is commercially available from Spectrum Laboratory Products Inc. of Gardena, Calif.; a dimethyl polysiloxane, such as Dow Chemicals Syltherm XLT, which is commercially available from the Dow Chemical Company of Midland, Mich.; an aromatic hydrocarbon, such as Dynalene MV, which is commercially available from Dynalene Heat Transfer Fluids of Whitehall, Pa.; and propylene glycol, which is commercially available from Mallinckrodt Baker, Inc., of Phillipsburg, N.J. With these types of heat transfer fluids, the balloon or device in which the fluid is held is preferably made from either a polyurethane or silicone material.

In one particularly preferred embodiment, hydrochlorofluorocarbons (HCFC's), such as Asahiklin AK-225 or AK-225 g (hereinafter referred to as "AK-225"), which are commercially available from the Asahi Glass Co., Ltd. (Chemicals Americas, Inc.), of Tokyo, Japan, can be used as the heat transfer fluid, such as the fluid used to inflate the balloon. In this case, the balloon or device in which the fluid is held is preferably made from a polyurethane material, but may be made from other materials that can stretch to conform to the shape of the cavity in which it is inserted when filled with pressurized fluid, such as silicone, urethane, custom blends, and the like. Alternatively, the balloon could be made from a less elastic material like PET or the like, and sized such that inflation provides an expansion of the balloon's shape, such as by repositioning folds of the material, thereby maximizing contact between the balloon and the uterine cavity. The balloon should also have lubricous surface properties which prevent the balloon from sticking to itself and also allow it to easily slide over the uterine wall to allow uniform contact with the endometrium when inflated. Preferably, the balloon material should be relatively thin to minimize the thermal conduction losses due to heat transfer that can occur with balloons having a relatively large thickness, such as greater than about 0.05 mm for example. In addition, the balloon material should not crack or otherwise degrade when subjected to the extremely cold temperatures required for the cryoablation procedure and the balloon material should be compatible with the heat transfer fluid.

However, it is understood that fluids having similar properties to that of AK-225 may also be used as the heat transfer fluid, such as a fluid having a low vapor pressure at room temperature, a fluid having a freezing point that is preferably lower than about −110 degrees C. and a boiling point that is greater than about 50 degrees C., and more preferably has a freezing point that is lower than about −130 degrees C. and a boiling point that is greater than about 60 degrees C. In any case, it is preferred that the boiling point be at least above room temperature so that the fluid remains a fluid and does not vaporize when subjected to temperatures near room temperature. The heat transfer material preferably also has a relatively low viscosity over the entire operating temperature range to avoid large pressure drops, particularly when the material is exiting the balloon as this may generate uncomfortably high pressure within the uterus. The fluid is also preferably chemically inert to prevent degradation of the balloon, fluid lines, valves, seals, and other system components. In order to allow electrical isolation of the patient from the ground, the fluid is preferably not conductive. Further the heat transfer fluid is preferably chemically stable to allow storage for long periods and sterilization if necessary by methods of heat and gamma irradiation, for example. It is also preferably not flammable, not at risk of degrading into flammable or toxic compounds if exposed to electricity or high temperatures, and is both biocompatible and environmentally friendly.

Fluids used in the balloon, such as AK-225, are particular advantageous in accordance with the devices and methods of the present invention because it can remain in its liquid state when subjected to the operating conditions of the system. That is, the fluid preferably remains a liquid even at extremely low temperatures to provide better heat transfer to the patient. This type of fluid is able to cause a desired range of about 5 mm to about 7 mm of ablated tissue thickness to reach a temperature of about −20 degrees C. (which is well above its freezing point) at its outside edge, which is sufficient for ablation under many circumstances. In addition, the fluid used in the balloon preferably also remains a liquid within the balloon to provide a more uniform transfer of cooling to the tissue in contact with the balloon. It is further desirable that the fluid remains a liquid at room temperature and at the highest operating temperatures inside the system, thereby facilitating low pressure circulation of the fluid, ease of fluid handling and safety from a lack of significantly pressurized components in the fluid circuit.

Any of the embodiments of a cold tip discussed above may optionally include some type of disposable protective barrier or layer that can slip over the portion of the device that will be inserted into the patient. Since the protective layer can be removed and discarded after the procedure is complete, the cleaning and sterilization of the cold tip between procedures can be minimized or eliminated and the tip can be used to perform multiple surgeries. The protective layer is preferably provided to be as thin as possible in order to not interfere with the cooling of the tissue that is to be ablated, but thick enough that it does not tear during the insertion of the probe into the patient or during the ablation process. In cases where the cold tip includes multiple fingers or extensions, the protective layer may include individual tips for each of the multiple fingers, or may include a single protective layer or cover that covers all of the multiple fingers. The same or similar materials and designs as the balloons described above can also be used for the disposable protective barriers of the cold tip, if desired.

The cold tips or probe tips described above and the devices to which they are attached can be designed and manufactured as a permanent part of the device such that once the device can no longer perform the desired surgical procedure, the entire device will be discarded. This may involve few or many uses of the equipment, depending on the device and the operating conditions in which it is used. For example, the use of protective covers can extend the life of the equipment. However, it is contemplated in accordance with the present invention that the probe tips used with a particular device instead be removable and replaceable in a "modular" type of system that allows the breaking of the refrigerant circuit to accept multiple probe tips of the same or different types. In this case, the probe tips could be disposable, thereby eliminating the need to sterilize the devices after each use. A modular system of this type preferably includes valving and storage reservoirs used to recover the refrigerant from the probe tip prior to detachment and evacuation of the probe tip after attachment.

For one example, the modular system includes a gas mix compressor that is used to transfer refrigerant from the probe tip to a storage reservoir during the detachment of the probe tip. The probe tip is then isolated with valves and residual gas in the probe can be vented to the atmosphere. A vacuum pump can then be used to evacuate the air in the system before reattaching the same or a different probe tip. Refrigerant can then be reintroduced to the probe tip by opening or activating the valves that were used to isolate the probe tip during its detachment from the system.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A modular cryoablation system for performing endometrial ablation, comprising:
   an elongated tubular cannula having a proximal end, a distal end, and a longitudinal axis;
   a probe tip comprising a center tube having an internal fluid path and at least two extensions that are each expandable and retractable outwardly relative to the longitudinal axis of the cannula and that each comprise an internal fluid path that is in fluidic communication with the internal fluid path of the center tube, wherein the probe tip is coupled to the distal end of the cannula, and wherein each of the extensions comprises a first end that extends from a distal end of the center tube and a second end spaced from the first end;
   a probe handle extending from the proximal end of the cannula and in fluidic communication with the internal fluid path of each of the extensions through the cannula and the center tube; and
   a source of compressed refrigerant fluidly connected to the probe handle.

2. The cryoablation system of claim 1, further comprising a sheath that can at least partially contain at least two extensions in a retracted position and wherein the sheath is moveable along the length of the cannula to expose at least a portion of the center tube and the extensions and allow the at least two extensions to rotate about their first ends.

3. The cryoablation system of claim 1, wherein the probe tip is coupled to the cannula by a coupling mechanism that fluidly isolates the fluid paths of the extensions from the probe handle and refrigerant source to create a closed first fluid system when the probe tip is detached from the cannula.

4. The cryoablation system of claim 3, wherein the coupling mechanism allows for fluidic communication between the probe handle and the probe tip through the cannula when the probe tip is attached to the cannula.

5. The cryoablation system of claim 1, wherein the at least two extensions of the probe tip comprise at least three elongated members.

6. The cryoablation system of claim 1, wherein the probe tip is removable and replaceable with a replacement probe tip for performing repeated endometrial ablation procedures.

7. The cryoablation system of claim 1, wherein the system provides refrigerant at a temperature that is sufficiently low to ablate a uterine lining when it is in the probe tip.

8. The cryoablation system of claim 1, wherein the probe tip is detachably coupled to the distal end of the cannula.

9. The cryoablation system of claim 1, wherein the probe tip is permanently coupled to the distal end of the cannula.

10. The cryoablation system of claim 1, wherein the first end of each of the extensions is hingedly attached to the distal end of the center tube.

11. The cryoablation system of claim 1, wherein the at least two extensions comprise a first extension and a second extension, and wherein the first end of each of the extensions is attached to the distal end of the center tube by a hinge mechanism comprising a spring element that biases the first and second extensions away from each other.

* * * * *